(12) United States Patent
Han et al.

(10) Patent No.: US 11,028,139 B2
(45) Date of Patent: Jun. 8, 2021

(54) RECOMBINANT PROTEIN FOR PREVENTING OR TREATING TISSUE FIBROSIS AND COMPOSITION FOR PREVENTING OR TREATING TISSUE FIBROSIS COMPRISING THE SAME

(71) Applicant: NEXEL CO., LTD., Seoul (KR)

(72) Inventors: Choong Seong Han, Seoul (KR); Dong Hun Woo, Seoul (KR); Gun Sik Cho, Daejeon (KR); Jeong Seong Kim, Hanam-si (KR); Geun Ho An, Seoul (KR); Hye Ryeon Jeon, Seongnam-si (KR)

(73) Assignee: NEXEL CO., LTD., Seoul (KR)

(*) Notice: Subject to any disclaimer, the term of this patent is extended or adjusted under 35 U.S.C. 154(b) by 0 days.

(21) Appl. No.: 15/994,323

(22) Filed: May 31, 2018

(65) Prior Publication Data

US 2018/0334486 A1 Nov. 22, 2018

Related U.S. Application Data

(63) Continuation of application No. PCT/KR2017/005150, filed on May 18, 2017.

(30) Foreign Application Priority Data

May 17, 2017 (KR) .................. 10-2017-0060995

(51) Int. Cl.
*A61K 38/17* (2006.01)
*C07K 14/47* (2006.01)
(Continued)

(52) U.S. Cl.
CPC ........ *C07K 14/485* (2013.01); *A61K 38/1709* (2013.01); *A61P 1/16* (2018.01); *C07K 14/47* (2013.01); *A61K 38/00* (2013.01)

(58) Field of Classification Search
CPC ............................ A61K 38/1709; C07K 14/47
See application file for complete search history.

(56) References Cited

U.S. PATENT DOCUMENTS

2006/0246095 A1* 11/2006 Peretz .................. C12N 15/62
424/277.1

FOREIGN PATENT DOCUMENTS

KR 10-2017-0013621 A 2/2017
WO WO 95/15171 * 6/1995
(Continued)

OTHER PUBLICATIONS

Atabai et al., J. Clin. Invest., 2009, vol. 119(12):3713-3722.*
(Continued)

*Primary Examiner* — Xiaozhen Xie
(74) *Attorney, Agent, or Firm* — Studebaker & Brackett PC

(57) ABSTRACT

The present invention relates to a recombinant protein for preventing or treating tissue fibrosis, which is based on milk fat globule-EGF factor 8 (MFG-E8) protein and comprises the amino acid sequence of SEQ ID NO: 1, and to a composition for preventing or treating tissue fibrosis, which comprises the recombinant protein. The level of the effect of preventing or treating tissue fibrosis by the recombinant protein of the present invention is significantly improved compared to that of conventional milk fat globule-EGF factor 8 (MFG-E8) protein, so that the level of tissue fibrosis can be restored to a level very close to that in normal tissue by the prevention and treatment of tissue fibrosis.

2 Claims, 5 Drawing Sheets
Specification includes a Sequence Listing.

NP-011: 225 a.a (SEQ ID NO: 1)

MPRPRLLAALCGALLCAPSLLVA (signal peptide)
LDICSKNPCHNGGLCEEISQEVRGDVFPSYTCTCLKGYAGNHCE (EGF-like domain)
TKCVEPLGMENGNIANSQIAASSVRVTFLGLQHWVPELARLNRAGMVNAWTPSSNDDNPWI
QVNLLRRMWVTGVVTQGASRLASHEYLKAFKVAYSLNGHEFDFIHDVNKKHKEFVGNWNKNAV
HVNLFETPVEAQYVRLYPTSCHTACTLRFELLGC (C1 domain)

(51) Int. Cl.
*C07K 14/485* (2006.01)
*A61P 1/16* (2006.01)
*A61K 38/00* (2006.01)

(56) References Cited

FOREIGN PATENT DOCUMENTS

WO    2015/025956 A1    2/2015
WO    2017/018698 A1    2/2017

OTHER PUBLICATIONS

An et al.: "Milk Fat Globule-EGF Factor 8, Secreted by Mesenchymal Stem Cells, Protects Against Liver Fibrosis in Mice"; Gastroenterology; Apr. 2017; pp. 1174-1186; vol. 152, No. 5; Republic of Korea.
Häggqvist et al.; "Medin: An integral fragment of aortic smooth muscle cell-produced lactadherin forms the most common human amyloid"; Proc. Natl. Acad. Sci.; Jul. 1999; pp. 8669-8674; vol. 96; USA.
Atabai et al.; "Mfge8 diminishes the severity of tissue fibrosis in mice by binding and targeting collagen for uptake by macrophages"; The Journal of Clinical Investigation; Dec. 2009; pp. 3713-3722; vol. 119; No. 12; USA.
O'Haese et al.; "The impact of MFG-E8 in chronic pancreatitis: potential for future immunotherapy?"; BMC Gastroenterology; 2013; pp. 1-9, http://www.biomedcentral.com/1471-230X/13/14.

\* cited by examiner

FIG. 1

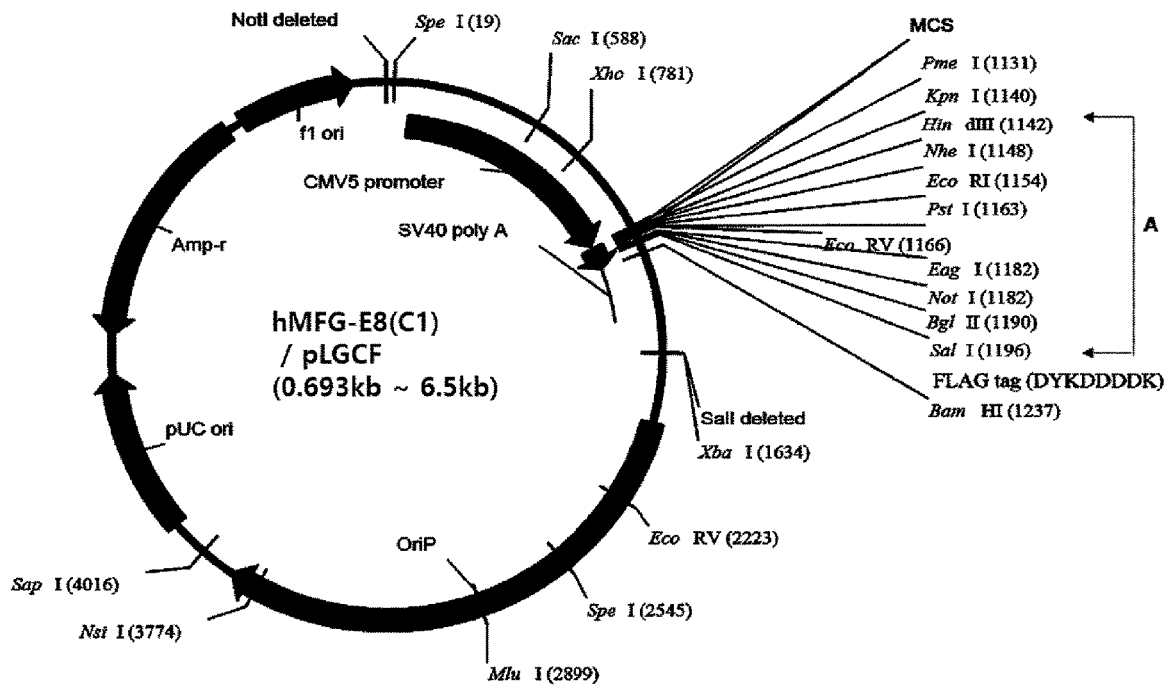

NP-011: EGF-like domain + C1 domain (SEQ ID NO: 2)

atgccgcgccccgcctgctggccgcgctgtgcggcgcgctgctctgcgcccccagcctcctcgtcgccctggatatctgttcca
aaaaccccctgccacaacggtggtttatgcgaggagatttcccaagaagtgcgaggagatgtcttcccctcgtacacctgcacgt
gccttaagggctacgcgggcaaccactgtgagacgaaatgtgtcgagccactgggcctggagaatgggaacattgccaact
cacagatcgccgcctcgtctgtgcgtgtgaccttcttgggtttgcagcattgggtcccggagctggcccgcctgaaccgcgcag
gcatggtcaatgcctggacacccagcagcaatgacgataaccccctggatccaggtgaacctgctgcggaggatgtgggtaac
aggtgtggtgacgcagggtgccagccgcttggccagtcatgagtacctgaaggccttcaaggtggcctacagccttaatgga
cacgaattcgatttcatccatgatgttaataaaaaaacacaaggagtttgtgggtaactggaacaaaaacgcggtgcatgtcaac
ctgtttgagacccctgtggaggctcagtacgtgagattgtaccccacgagctgccacacggcctgcactctgcgctttgagctac
tgggctgt

NP-011: 225 a.a (SEQ ID NO: 1)

MPRPRLLAALCGALLCAPSLLVA (signal peptide)
LDICSKNPCHNGGLCEEISQEVRGDVFPSYTCTCLKGYAGNHCE (EGF-like domain)
TKCVEPLGMENGNIANSQIAASSVRVTFLGLQHWVPELARLNRAGMVNAWTPSSNDDNPWI
QVNLLRRMWVTGVVTQGASRLASHEYLKAFKVAYSLNGHEFDFIHDVNKKHKEFVGNWNKNAV
HVNLFETPVEAQYVRLYPTSCHTACTLRFELLGC (C1 domain)

SEQUENCE LISTING

<160> NUMBER OF SEQ ID NOS: 8

<210> SEQ ID NO 1
<211> LENGTH: 225
<212> TYPE: PRT
<213> ORGANISM: Artificial Sequence
<220> FEATURE:
<223> OTHER INFORMATION: Protein for curing tissue fibrosis including liver fibrosis

<400> SEQUENCE: 1

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Met Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys
225

<210> SEQ ID NO 2
<211> LENGTH: 675
<212> TYPE: DNA
<213> ORGANISM: Artificial Sequence
<220> FEATURE:
<223> OTHER INFORMATION: DNA fragment encoding NP-011

<400> SEQUENCE: 2
atgccgcgcc ccgcctgct  ggccgcgctg tgcggcgcgc tgctctgcgc cccagcctc      60 ctcgtcgccc tggatatctg ttccaaaaac ccctgccaca acggtggttt atgcgaggag    120
atttcccaag aagtgcgagg agatgtcttc ccctcgtaca cctgcacgtg ccttaagggc    180
tacgcgggca accactgtga gacgaaatgt gtcgagccac tgggcctgga gaatgggaac    240
attgccaact cacagatcgc cgcctcgtct gtgcgtgtga ccttcttggg tttgcagcat    300
tgggtcccgg agctggcccg cctgaaccgc gcaggcatgg tcaatgcctg gacacccagc    360

```
agcaatgacg ataacccctg gatccaggtg aacctgctgc ggaggatgtg ggtaacaggt    420
gtggtgacgc agggtgccag ccgcttggcc agtcatgagt acctgaaggc cttcaaggtg    480
gcctacagcc ttaatggaca cgaattcgat ttcatccatg atgttaataa aaaacacaag    540
gagtttgtgg gtaactggaa caaaaacgcg gtgcatgtca acctgtttga daccccctgtg   600 gaggctcagt acgtgagatt gtaccccacg agctgccaca cggcctgcac tctgcgcttt    660
gagctactgg gctgt                                                    675
```

```
<210> SEQ ID NO 3
<211> LENGTH: 24
<212> TYPE: DNA
<213> ORGANISM: Artificial Sequence
<220> FEATURE:
<223> OTHER INFORMATION: sense primers for COL1A1 used for RT-PCR-

<400> SEQUENCE: 3
caatgcaatg aagaactgga ctgt                                           24

<210> SEQ ID NO 4
<211> LENGTH: 24
<212> TYPE: DNA
<213> ORGANISM: Artificial Sequence
<220> FEATURE:
<223> OTHER INFORMATION: antisense primers for COL1A1 used for RT-PCR-

<400> SEQUENCE: 4
tcctacatct tctgagtttg gtga                                           24

<210> SEQ ID NO 5
<211> LENGTH: 20
<212> TYPE: DNA
<213> ORGANISM: Artificial Sequence
<220> FEATURE:
<223> OTHER INFORMATION: sense primers for COL1A2 used for RT-PCR-

<400> SEQUENCE: 5
gcagggttcc aacgatgttg                                                20

<210> SEQ ID NO 6
<211> LENGTH: 21
<212> TYPE: DNA
<213> ORGANISM: Artificial Sequence
<220> FEATURE:
<223> OTHER INFORMATION: antisense primers for COL1A2 used for RT-PCR-

<400> SEQUENCE: 6
gcagccatcg actaggacag a                                              21

<210> SEQ ID NO 7
<211> LENGTH: 19
<212> TYPE: DNA
<213> ORGANISM: Artificial Sequence
<220> FEATURE:
<223> OTHER INFORMATION: sense primers for GADPH used for RT-PCR-

<400> SEQUENCE: 7
gttgtctcct gcgacttca                                                 19

<210> SEQ ID NO 8
<211> LENGTH: 19
<212> TYPE: DNA
<213> ORGANISM: Artificial Sequence
<220> FEATURE:
```

```
<223> OTHER INFORMATION: antisense primers for GAPDH used for RT-PCR-

<400> SEQUENCE: 8
ggtggtccag ggtttctta                                              19
```

RECOMBINANT PROTEIN FOR PREVENTING OR TREATING TISSUE FIBROSIS AND COMPOSITION FOR PREVENTING OR TREATING TISSUE FIBROSIS COMPRISING THE SAME

REFERENCE TO AN ELECTRONIC SEQUENCE LISTING

The contents of the electronic sequence listing (2020-08-24_Sequence_Listing.txt; Size: 4,132 bytes; and Date of Creation: Aug. 24, 2020) has been submitted electronically via EFS-Web and is herein incorporated by reference in its entirety.

CROSS-REFERENCE TO RELATED APPLICATIONS

This application is a Continuation Application of PCT International Application No. PCT/KR2017/005150, which was filed on May 18, 2017, and which claims priority from Korean Patent Application No. 10-2017-0060995 filed with the Korean Intellectual Property Office on May 17, 2017. The disclosures of the above patent applications are incorporated herein by reference in their entirety.

TECHNICAL FIELD

The present invention relates to a recombinant protein for preventing or treating tissue fibrosis, which is based on milk fat globule-EGF factor 8 (MFG-E8) protein, and to a composition for preventing or treating tissue fibrosis, which comprises the same.

BACKGROUND ART

Liver transplantation is the only method for treatment of chronic liver diseases, including liver fibrosis and cirrhosis, but it is difficult to secure donors for liver transplantation. For this reason, drugs containing compounds, including ursodeoxycholic acid (UDCA) and silymarin, are currently used for treatment of chronic liver diseases, excluding liver transplantation.

However, these compounds are merely Therapeutic supplements exhibiting the effect of preventing liver cell damage, and do not act as fundamental therapeutic agents for treating liver diseases. Thus, there is an urgent need to develop effective therapeutic agents for treating chronic liver diseases.

In addition, in recent years, compounds, including S-adenosylmethionine, Rosiglitazone, Pioglitazone, Losartan and the like, which show anti-fibrosis effects, have been in clinical trials. However, these compounds also did not show significant disease-alleviating effects in clinical trials. Thus, there is an urgent need to develop drugs capable of treating tissue fibrosis including chronic liver diseases.

In connection with this, the applicant of the present invention disclosed a composition for preventing or treating tissue fibrosis in the liver, lung, kidney, brain, heart, diaphragm or the like, in which the composition has the properties of reducing collagen expression induced by the TGFβ/Smad signaling pathways, alleviating liver fibrosis by inhibition of the activation of hepatic stellate cells, reducing the degree of liver fibrosis in liver fibrosis disease models, and inhibiting the activation of hepatic stellate cells cultured in vitro (Korean Patent Application Publication No. 10-2017-0013621, entitled "Composition for preventing or treating tissue fibrosis using milk fat globule-EGF factor 8 (MFG-E8).

This protein therapeutic agent has advantages over conventional low-molecular compounds in that it is biocompatible, causes less side effects, and is easily mass-produced and quality-controlled, and the clinical trial success rate of new drugs is about 2-fold higher.

However, the applicant has made efforts to further improve the level of prevention or treatment function provided by the conventional composition for preventing or treating tissue fibrosis using milk fat globule-EGF factor 8 (MFG-E8), thereby improving the function of anti-tissue fibrosis to a level very close to the normal level at which tissue fibrosis does not occur.

DISCLOSURE

Technical Problem

The present invention has been made in order to solve the above-described problem, and an object of the present invention is to provide a recombinant protein which has an improved effect of preventing or treating tissue fibrosis compared to the conventional milk fat globule-EGF factor 8 (MFG-E8) protein, and thus has anti-tissue fibrosis function so that the level of tissue fibrosis can be restored to a level very close to the normal level, and a composition comprising the recombinant protein.

Technical Solution

To achieve the above object, the present invention provides a recombinant protein for preventing or treating tissue fibrosis, which is based on milk fat globule-EGF factor 8 (MFG-E8) protein and comprises the amino acid sequence of SEQ ID NO: 1.

The present invention also provides a composition for preventing or treating tissue fibrosis, comprising, as an active ingredient, a recombinant protein which is based on milk fat globule-EGF factor 8 (MFG-E8) protein and comprises the amino acid sequence of SEQ ID NO: 1.

In another aspect, the present invention provides a gene encoding a recombinant protein which is based on milk fat globule-EGF factor 8 (MFG-E8) protein and which comprises the amino acid sequence of SEQ ID NO: 1.

In still another aspect, the present invention provides a recombinant vector comprising a gene encoding a recombinant protein which is based on milk fat globule-EGF factor 8 (MFG-E8) protein and which comprises the amino acid sequence of SEQ ID NO: 1.

Advantageous Effects

The present invention has the following effects.

First, the level of the effect of preventing or treating tissue fibrosis by the recombinant protein of the present invention is significantly improved compared to that of the conventional milk fat globule-EGF factor 8 (MFG-E8) protein, so that the level of tissue fibrosis can be restored to a level very close to that in normal tissue by the prevention and treatment of tissue fibrosis.

Second, the present invention may provide a composition for preventing or treating tissue fibrosis, which is more biocompatible and causes less side effects, compared to conventional agents for preventing or treating tissue fibrosis, which comprise low-molecular compounds.

Third, the present invention may provide a composition for preventing or treating tissue fibrosis, which is easily mass-produced and quality-controlled.

Fourth, through the above-described effects, the present invention may be used as a fundamental therapeutic agent for chronic liver diseases, which is not a simple supplement for preventing or treating tissue fibrosis.

DESCRIPTION OF DRAWINGS

FIG. 1 shows the structure of a backbone vector (pLGCF vector) in which a gene encoding NP-011 of the present invention may be inserted into portion A and which is for transfection into HEK293.

FIG. 2 shows the DNA nucleotide sequence of a gene which encodes NP-011 of the present invention and which may be inserted into portion A shown in FIG. 1.

FIG. 9 shows the amino acid sequence of NP-011 of the present invention.

BEST MODE

Hereinafter, preferred examples of the present invention will be described in further detail with the accompanying drawings, but already known technical features will be omitted or compressed for briefness of description.

1. Description of Method for Cloning and Purification of Recombinant Protein NP-011 Based on Milk Fat Globule-EGF Factor 8 (MFG-E8) Protein Procedures for cloning and purification of the recombinant protein NP-011 of the present invention, which is based on milk fat globule-EGF factor 8 (MFG-E8) protein, will now be described in detail with reference to FIGS. 1 to 4.

First, in order to improve the structure of MFG-E8 protein, an MFG-E8 (NM_005928) human cDNA clone (Origene, Cat. No. RG217163) was purchased, and PCR was performed using the clone as a template, thereby producing a DNA fragment as shown in FIG. 2.

Next, cloning was performed to insert the DNA fragment of FIG. 2, obtained by PCR amplification, into the HindIII and SalI restriction enzyme sites (portion A in FIG. 1) of a pLGCF vector which is an mammalian expression vector and which has the structure shown in FIG. 1.

Then, the plasmid DNA was extracted and transfected into HEK 293 cells. After 2 days, the culture was collected and subjected to immunoprecipitation (IP), and the expression of the protein corresponding to NP-011 was analyzed by Western blotting.

In addition, the plasmid DNA whose expression was confirmed was obtained in large amounts by maxi prep, and then a large amount of the plasmid DNA was transfected into prepared HEK 293 cells, and mass production of the protein corresponding to NP-011 was performed.

Specifically, Corning 10-chamber CellSTACK cell culture chamber was prepared, and HEK 293 cells were applied thereto. Then, 1600 μg of the plasmid DNA and 3200 μl of transfection reagents were mixed at room temperature for 15 minutes and transfected into the HEK 293 cells. At 4 hours after the transfection, the medium was replaced, and the cells were additionally cultured for 6 days. The culture was collected at 2-day intervals (collected a total of 3 times), and the protein was purified from the collected culture by an affinity method.

Because FLAG gene was expressed in the C-terminal region of each protein, the protein purification was performed by binding only the target protein to FLAG affinity resin, followed by washing with washing buffer to remove proteins other than the target protein.

Next, only the pure target protein was extracted using elution buffer, after which SDS-PAGE was performed to confirm the finally obtained protein, and the production and purity of the target protein were analyzed by Coomassie blue staining and Western blotting.

The Western blotting was performed using anti-FLAG antibody, and the concentration of the finally obtained protein was measured using a micro BCA kit (Thermo). The results are shown in FIG. 3.

Figures 3, 4:
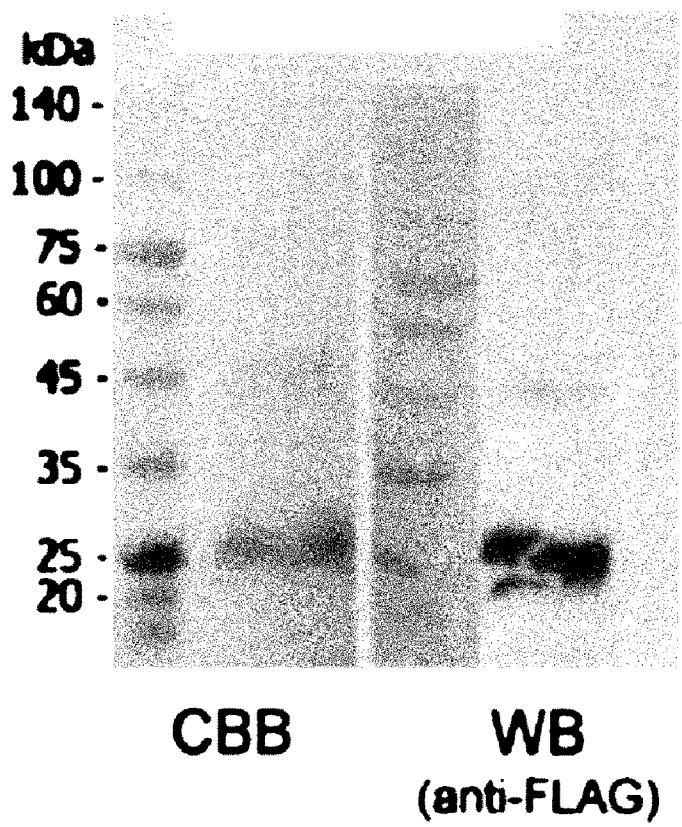
FIG. 3 shows the results obtained by transfecting a pLGCF vector comprising a gene encoding NP-011 of the present invention into HEK293, and then electrophoresing isolated and purified NP-011, followed by Coomassie brilliant blue (CBB) staining and Western blotting.

The recombinant protein NP-011, obtained by the cloning and purification procedures as described above and based on the milk fat globule-EGF factor 8 (MFG-E8) protein, is shown in FIG. 4 or represented by SEQ ID NO: 1.

2. Description of Test Results for Verification of Tissue Anti-fibrosis Effect of Recombinant Protein NP-011 Based on Milk Fat Globule-EGF Factor 8 (MFG-E8) Protein Next, in collection with the recombinant protein NP-011 of the present invention, which is based on the milk fat globule-EGF factor 8 (MFG-E8) protein and comprises the amino acid sequence of SEQ ID NO: 1, whether the recombinant protein would exhibit the effect of preventing or treating tissue fibrosis and whether the effect of the recombinant protein would be improved were examined by tests. In the tests, the following experimental methods were used for the purpose of defining properties and the like by means obvious to those skilled in the art.

(1) Construction of Liver Fibrosis Animal Models and Protein Injection

First, 5-week old C57/BL6 male mice were used to establish liver fibrosis mouse models. Specifically, liver fibrosis models were constructed by injecting 200 mg/kg of thioacetamide (TAA) into 5-week old C57/BL6 male mice. More specifically, liver fibrosis models were constructed by intraperitoneally injecting 200 mg/kg of thioacetamide (TAA) into mice three times a week for 8 weeks.

After the liver fibrosis mouse models were constructed by injecting thioacetamide (TAA) for 8 weeks, 160 μg/kg of NP-011 was injected intraperitoneally into the mice on the next day.

As a normal control group, mice (normal) not injected with thioacetamide (TAA) were used, and a disease control group, mice (Sham), not injected with the protein after injected with thioacetamide (TAA) for 8 weeks, were used.

For a positive control group, liver fibrosis mouse models were constructed by injecting thioacetamide (TAA) for 8 weeks, and then injected with 160 μg/kg of MFG-E8 (purchased from R&D System).

(2) Test for Analysis of Degree of Fibrosis in Liver Fibrosis Animal Models

3 Days after the protein injection as described above was performed, mouse liver tissue was collected from all the control groups and the test group, and the degree of fibrosis in the mouse liver was analyzed.

From a portion of the liver tissue dissected from each animal model, RNA was extracted for analysis of fibrosis-related marker genes (COL1A1 and COL1A2). For tissue examination, the remaining liver tissue was fixed in 4% PFA, and then a paraffin block was prepared and cut to a thickness of 4 μm. The degree of fibrosis in the liver tissue was analyzed by H & E staining and Sirius red staining.

For the H & E staining, hematoxylin and eosin (purchased from Sigma) were used, and for the Sirius red staining, a Picro Siris Red Stain Kit (purchased from Sigma) was used.

Figure 5:
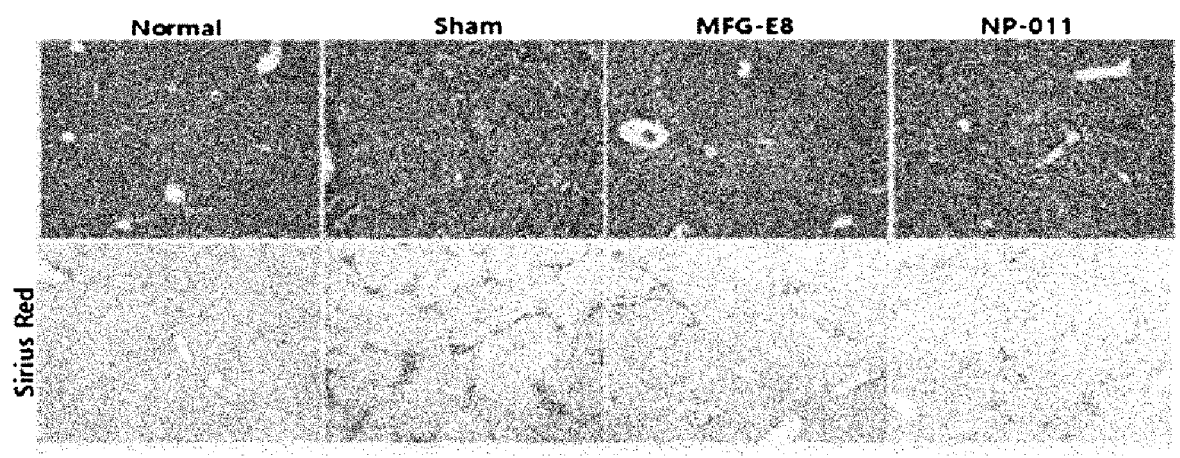
FIG. 5 depicts images showing the results of staining the liver tissues of a normal group, a disease control group (Sham), an MFG-E8-applied group and an NP-011-applied group.

As shown in FIG. 5, the results show that the degree of liver tissue damage and the degree of collagen accumulation in the liver tissue in the test animals injected with NP-011 were significantly alleviated compared to those in the disease control group, and the degree of the alleviation was particularly restored to a level very similar to that in the normal group.

Meanwhile, for analysis of fibrosis-related marker genes in the liver tissue dissected from each animal model, RNA was obtained using TRIzol reagent and subjected to reverse transcription using a reverse transcription system (Promega Corp., USA). PCR amplification was performed under the following conditions: 94° C. for 5 min; 35 cycles (each consisting of 94° C. for 30 sec, 50 to 57° C. for 30 sec and 72° C. for 30 sec); and 72° C. for 10 min.

Specifically, RT-PCR analysis was performed using SYBR Green PCR Master Mix (Applied Biosystems, USA). The PCR reactant consisted of 25 μl comprising 12.5 μl of SYBR Green PCR Master Mix, 0.8 μl of 10 mM each primer, 10.4 μl of distilled water and 0.5 μl of template cDNA and was amplified under conditions suitable for each primer. The relative expression level of each gene was measured by normalization using GAPDH. The sequences of the primers used are shown in Table 1 below.

RNA was extracted from the dissected liver tissue, and the expression patterns of fibrosis markers (COL1A1 and COL1A2) were compared. As a result, as shown in FIGS. 6 and 7, the recombinant proteins corresponding to NP-011 all had the effect of reducing collagen accumulation compared to that in the disease control group (Sham).

Figure 6:
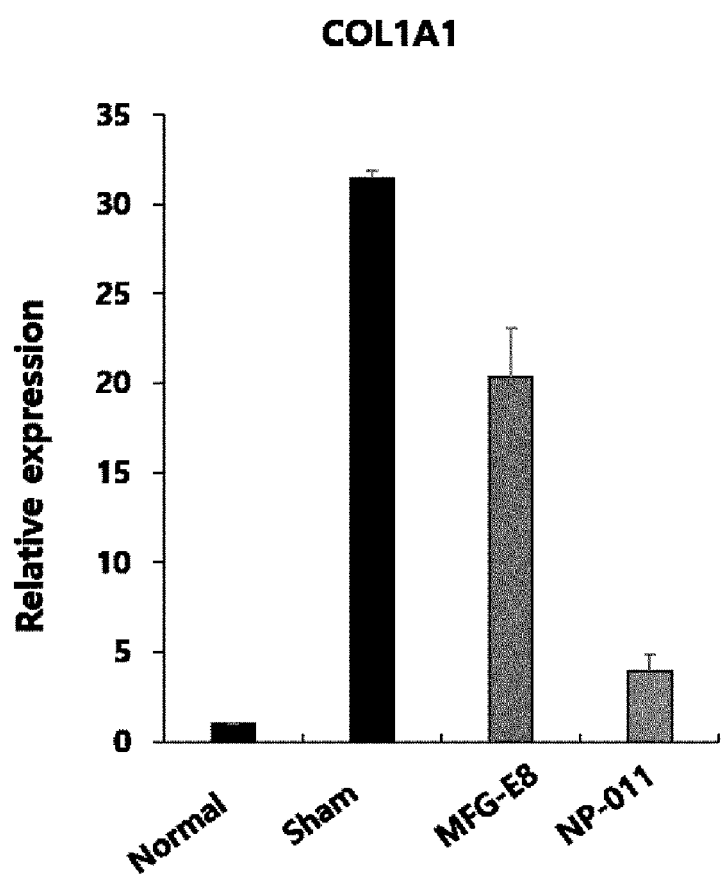
FIG. 6 shows the results of analyzing the expression patterns of COL1A1 in the liver tissues of a normal group, a disease control group (Sham), an MFG-E8-applied group and an NP-011-applied group.

In particular, as can be seen in FIG. 6 regarding COL1A1, the application of NP-011 degraded accumulated collagen to a level which was significantly different from that in the MFG-E8 protein-applied group and which was very similar to that in the normal group. This indicates that NP-011 shows an about 4-fold improved effect compared to the MFG-E8 protein.

Figure 7:
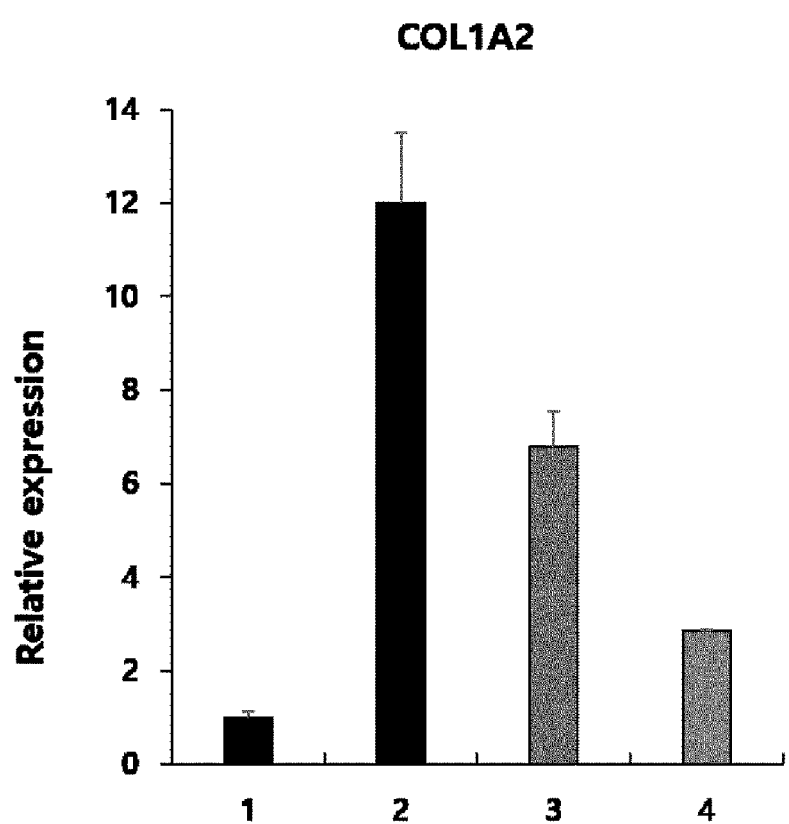
FIG. 7 shows the results of analyzing the expression patterns of COL1A2 in the liver tissues of a normal group, a disease control group (Sham), an MFG-E8-applied group and an NP-011-applied group.

In addition, as can be seen in FIG. 7 regarding COL1A2, the application of NP-011 degraded accumulated collagen to a level which was significantly different from that in the MFG-E8 protein-applied group and which was very similar to that in the normal group. This indicates that NP-011 shows an about 2.4-fold improved effect compared to the MFG-E8 protein.

As described above, the recombinant protein NP-011, based on the milk fat globule-EGF factor 8 (MFG-E8) protein and having the amino acid sequence shown in FIG. 4 or SEQ ID NO. 1, shows a significant improvement in the effect of preventing and treating tissue fibrosis (anti-tissue fibrosis ability), compared to the conventional milk fat globule-EGF factor 8 (MFG-E8) protein.

In the present invention, the tissue to which the effect of preventing and treating tissue fibrosis (anti-tissue fibrosis ability) can be provided by the above-described recombinant protein NP-011 is particularly represented by liver tissue, but is not limited thereto and may include various tissues (e.g., lung, salivary glands, etc.) in which in vivo tissue fibrosis may occur.

More specifically, from the fact that the level of improvement by NP-011 can be restored to the level in normal tissue by providing the effect of preventing and treating tissue fibrosis (anti-tissue fibrosis ability), it can be seen that NP-011 is not a simple supplement for preventing or treating tissue fibrosis, but is most suitable for use in the fundamental treatment of chronic liver diseases.

The embodiments disclosed in the present invention are not intended to limit the technical idea of the present invention, but are intended to explain the present invention, and the scope of the technical idea of the present invention is not limited to these embodiments. Therefore, the scope of the present invention to be protected should be interpreted based on the appended claims, and all the technical ideas equivalent thereto shall be interpreted as falling within the scope of the present invention to be protected.

TABLE 1

| Gene | Forward (5'→3') | Reverse (5'→3') | Product size (b.p.) |
| --- | --- | --- | --- |
| COL1A1 | CAATGCAATGAAGAACTGGACTGT (SEQ ID NO: 3) | TCCTACATCTTCTGAGTTTGGTGA (SEQ ID NO: 4) | 105 |
| COL1A2 | GCAGGGTTCCAACGATGTTG (SEQ ID NO: 5) | GCAGCCATCGACTAGGACAGA (SEQ ID NO: 6) | 76 |
| GAPDH | GTTGTCTCCTGCGACTTCA (SEQ ID NO: 7) | GGTGGTCCAGGGTTTCTTA (SEQ ID NO: 8) | 184 |

The invention claimed is:

1. An isolated recombinant protein for preventing or treating tissue fibrosis, the recombinant protein consists of the amino acid sequence of SEQ ID NO: 1, which is a fragment of human milk fat globule-EGF factor 8 (MFG-E8) protein.

2. A composition for preventing or treating tissue fibrosis, which comprises the recombinant protein of claim 1.

* * * * *